United States Patent [19]

Eason et al.

[11] Patent Number: 5,617,971
[45] Date of Patent: Apr. 8, 1997

[54] DEVICE FOR ADMINISTERING SINGLE DOSES OF A MEDICAMENT

[75] Inventors: Stephen W. Eason, Redgrave; Clive P. A. Catterall, Wantage; Roger W. Clarke, Histon, all of United Kingdom

[73] Assignee: Lipha SA, Lyons, Cedex, France

[21] Appl. No.: 442,674

[22] Filed: May 17, 1995

[30] Foreign Application Priority Data

May 17, 1994 [GB] United Kingdom ............... 9409852

[51] Int. Cl.$^6$ .................................................. G07F 11/72
[52] U.S. Cl. ................................. 221/31; 128/203.21
[58] Field of Search ................................. 221/30, 31, 25, 221/26; 128/203.12, 203.21, 203.15; 601/41

[56] References Cited

U.S. PATENT DOCUMENTS 5,207,217 5/1993 Cocozza et al. ............... 128/203.15
5,415,162 5/1995 Casper et al. .................. 128/203.21

Primary Examiner—Kenneth Noland
Attorney, Agent, or Firm—Lee, Mann, Smith, McWilliams, Sweeney & Ohlson

[57] ABSTRACT

A device for dispensing single doses of powdered medicament has a housing for holding a container which has a number of sealed apertures containing individual encapsulating doses of medicament. The container can move relative to the housing to allow each aperture in succession to be brought into registry with an airway which communicates with a mouthpiece. The device includes a piercing member, such as a pin, which can be inserted into a selected aperture to break its respective seals. The configuration and movement of the pin are such that this action expels substantially no powder from the aperture.

15 Claims, 17 Drawing Sheets

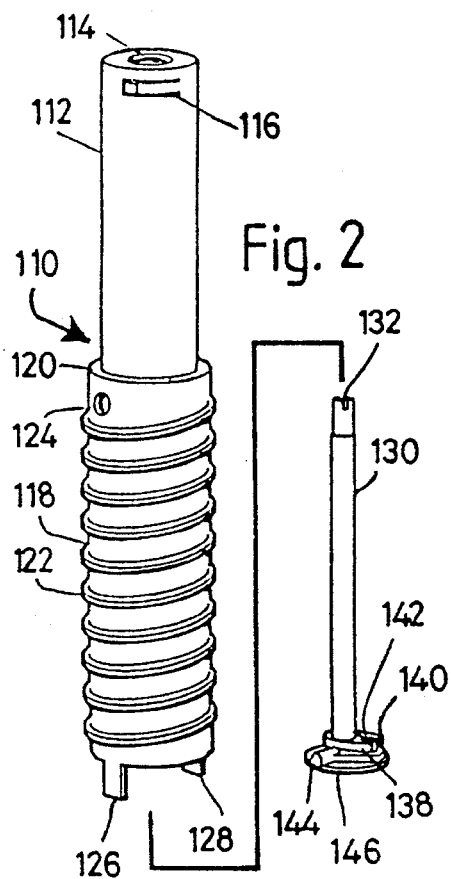
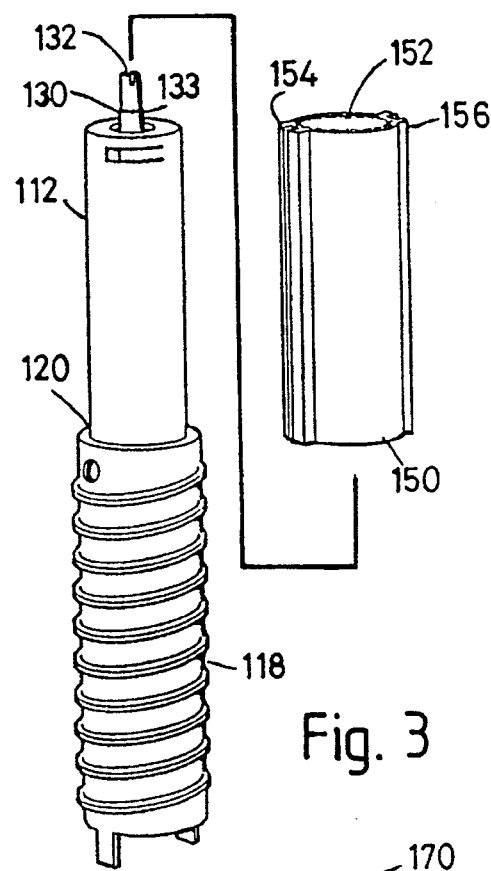
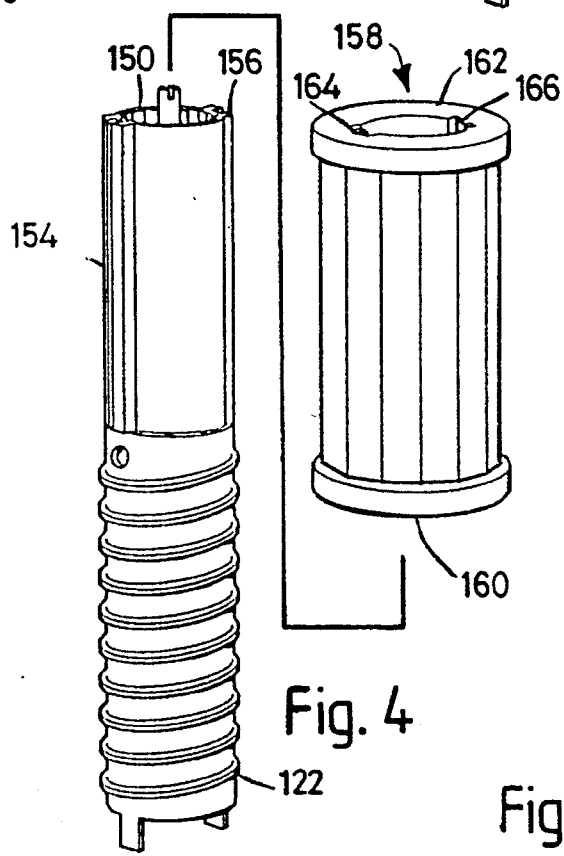
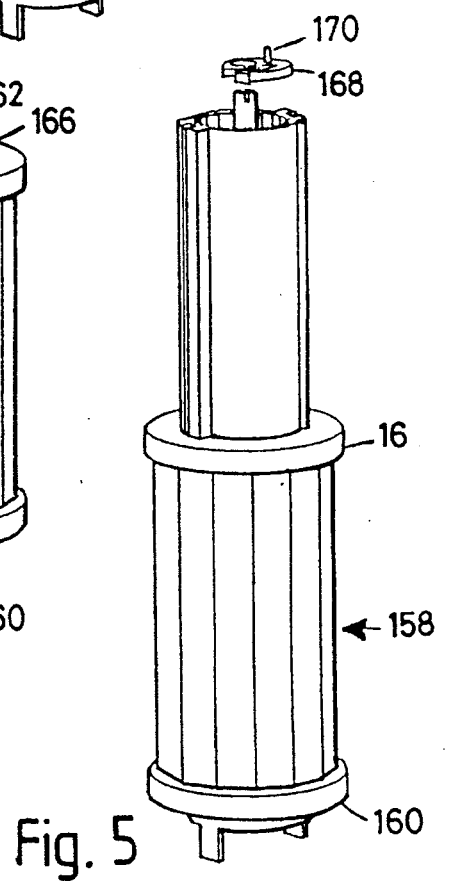

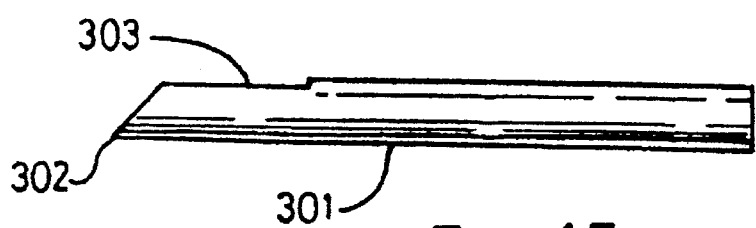
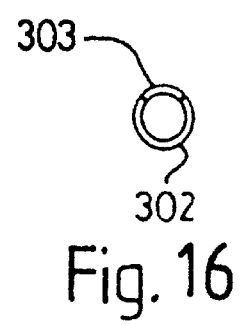
Fig. 15
Fig. 16
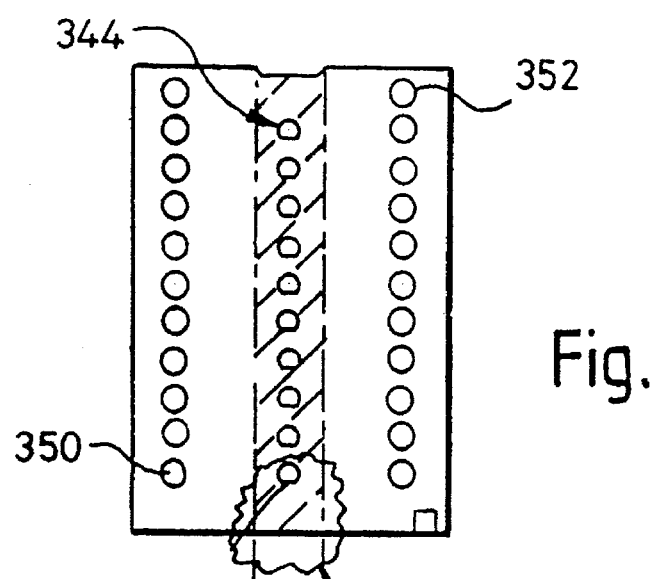
Fig. 17A
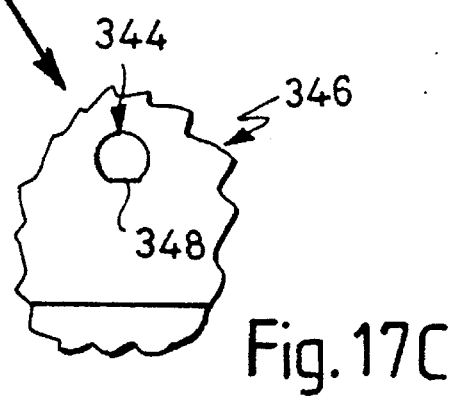
Fig. 17C
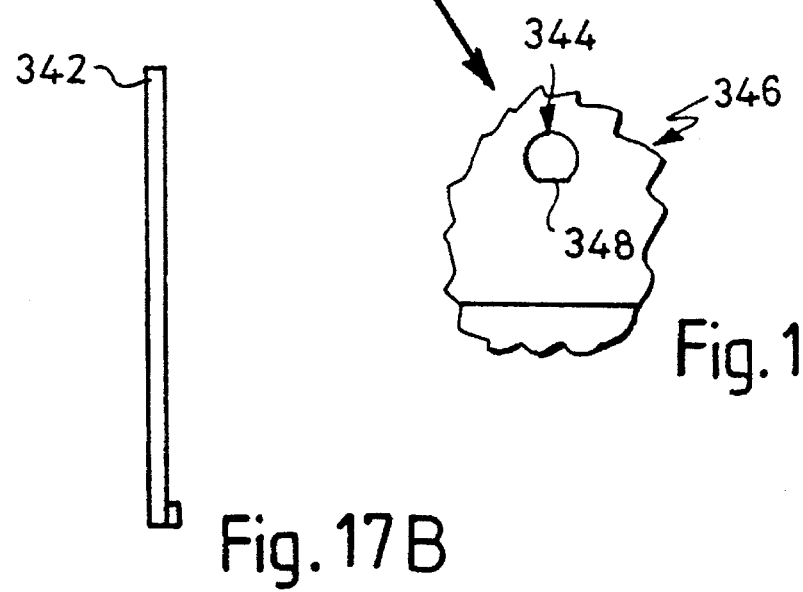
Fig. 17B

DEVICE FOR ADMINISTERING SINGLE DOSES OF A MEDICAMENT

FIELD OF THE INVENTION

This invention relates to dispensing devices, in particular devices for dispensing single doses of a medicament, and to a cartridge for use in such a device.

BACKGROUND OF THE INVENTION

It is known to treat certain respiratory problems, particularly asthma, with a pharmacologically active compound which is in a finely divided particulate form, and which is administered by inhalation. One known inhaler for dispensing such material is shown in UK Patent specification No GB2178965 (Glaxo Group Limited), and comprises a circular carrier which includes a number of blisters in each of which a respective dose of material is encapsulated. When a dose is to be administered, a user moves a slider which operates indexing means for bringing the blisters in succession into registry with an airway. The user then pivots a separate handle which ruptures the blister in registry with an airway to allow the medicament therein to be self administered by the user inhaling through a mouthpiece which communicates with the airway.

However, if a user operates the piercing and indexing mechanisms a number of times without inhaling through the mouthpiece, medicament can build up in the airway which results in the user taking too large a dose when he or she next inhales on the mouthpiece.

In addition, the need to operate the indexing means and the piercing mechanism separately can make the device awkward to use.

SUMMARY OF THE INVENTION

According to a first aspect of the invention, there is provided a device for dispensing single doses of a finely divided solid medicament from a container having a plurality of apertures, each of which holds a respective one of said doses and is sealed by two opposed seals, the device comprising a housing for holding the container, the housing having an outlet and an airway which communicates with the outlet and being configured to allow the container to move relative thereto to bring each aperture in succession into registry with the airway, wherein the device includes a piercing member moveable from a retracted position in which it is positioned clear of the apertures, into an extended position in which it extends through an aperture, said movement causing the piercing member to rupture first one and then the other of the opposed seals, whilst expelling substantially no medicament from that aperture.

Thus, if the user operates the device to pierce the seals of an aperture, but then does not inhale through the mouthpiece when that aperture is in registry with the airway, the material will tend to remain in the aperture. That material will not subsequently reach the mouthpiece when a dose is being administered from another aperture since the first said aperture will by then no longer be in registry with the airway.

Preferably, the piercing member comprises a pin which may to advantage be hollow. In the latter case, the forward end of the pin is preferably so shaped as to create in the seals flaps which can hinge away from their respective aperture to allow the contents of that aperture to be discharged. The housing may to advantage include means which hinge the flaps back towards the aperture as it is moved out of registry with the airway, thus further reducing the tendency for any remaining material in that aperture not to be subsequently expelled.

If the pin is hollow, it preferably has an axial slot at its forward end so that the forward end of the pin is substantially c-shaped, when the pin is viewed end on.

The device conveniently includes indexing means for bringing each aperture in succession into registry with the airway and a common actuating member linked to both the indexing means and to piercing means for extending and retracting the pin so that manipulation of the actuating member by the user both operates the indexing means and ruptures the seals of an aperture.

The common actuating member thus facilitates the operation of the device.

Preferably, the pin is so positioned as to rupture the seals of an aperture while the latter is in registry with the airway.

According to a second aspect of the invention, there is provided a device as aforesaid and a container having a plurality of sealed apertures, each holding a respective dose of medicament, the container being held within the housing of the device and being moveable to bring each aperture in succession into registry with the airway and the piercing member being operable to rupture the seals of each aperture whilst expelling substantially no medicament therefrom.

Preferably, the apertures are all sealed by two opposing pieces of sheet material bonded to the container.

Preferably, where the piercing member is operable to create said flaps in the sheet material, each aperture is flattened in the region where the hinges for the flaps are formed.

It has been found that this reduces the amount of residual material left in an aperture after the respective dose has been dispensed and thus reduces waste.

The container may be constituted by a substantially flat plate, or may be cylindrical.

Where the container is cylindrical, the actuating member preferably comprises a rotary member, rotation of which alternately causes the indexing means to rotate the container within the device and the pin to break the seals of an aperture.

Preferably, the device includes stop means for defining the maximum extent of allowable rotation of the rotary member.

Conveniently, rotation of the rotary member from one to the other of the two positions defined by the end stops causes the pin to pierce a seal, whilst rotation of the rotary member in the opposite sense into said one position causes the indexing means to rotate the container.

The indexing means preferably comprises a ratchet action mechanism operable to rotate the container in one sense only in response to reciprocating rotation of the rotary member.

Preferably, with a cylindrical container loaded into the device, the pin is situated in use within the volume defined by the inner periphery of the container.

Preferably, the indexing means is connected to the rotary member through lost motion means, so arranged as to prevent the indexing means moving the tubular container while the piercing member is being inserted into and/or withdrawn from a compartment.

Preferably, the rotary member is connected to a shaft which is in turn connected to the pin through linkage means comprising a crank arm pivotally attached to the pin so that the rotation of the shaft causes substantially linear motion of the pin.

The invention also lies in a cartridge for use in a device as aforesaid, the cartridge comprising a container for containing said doses, and may incorporate at least one of said piercing and indexing means.

The invention also lies in a device for dispensing single doses of a powdered medicament from a container having a plurality of sealed compartments, each containing a respective dose of medicament to be discharged through an outlet passage of the device, the device comprising indexing means operable to bring the outlet passage and successive compartments into registry with each other, and piercing means operable to break the seal on each compartment in succession, to enable material to be discharged therefrom, wherein the piercing means and indexing means are connected to a common manually operable actuating member, by means of which both the piercing means and the indexing means are operated.

The common actuating member enables the device to be of a relatively compact design, and allows the device to be used more easily than would be the case if, for example, a separate actuating member were required for each of the indexing means and the piercing means.

BRIEF DESCRIPTION OF THE DRAWINGS

The invention will now be described by way of example only, with reference to the accompanying drawings, which show two embodiments of dispenser in accordance with the invention, one of which has a cartridge assembly (which includes a tubular container) mounted within a housing, and in which;

FIGS. 2–5 are exploded isometric views of various components of the cartridge for that dispenser;

FIG. 15 is a side view of a component of both embodiments of dispenser;

FIG. 16 is an end view of the component shown in FIG. 15;

FIGS. 17A and 17B show a container for use with the dispenser in third angle projection;

FIG. 17C shows a part of the container as shown in FIG. 17A to an enlarged scale;

DETAILED DESCRIPTION

Figure 1:
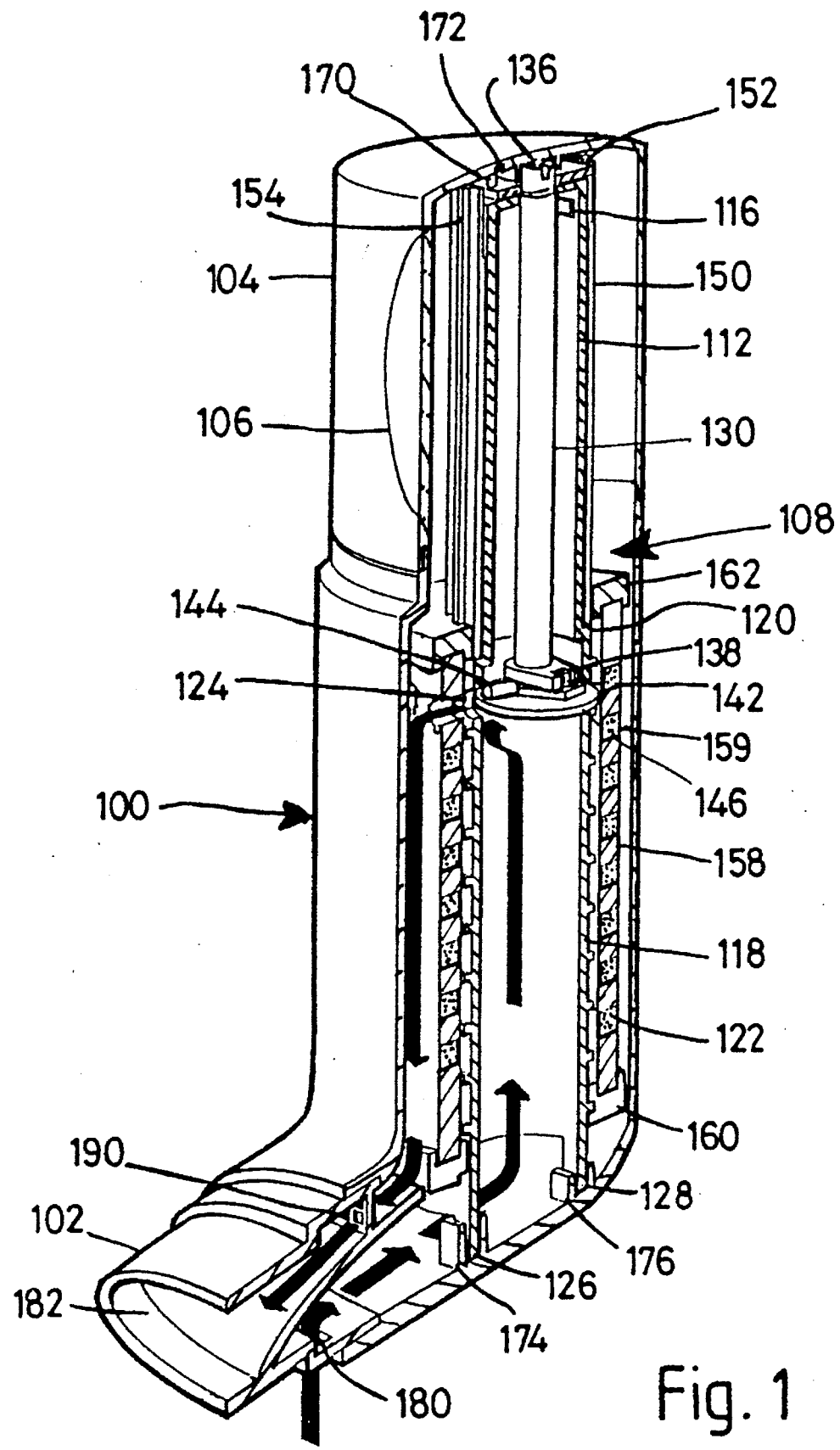
FIG. 1 is a partially cut away isometric view of the first embodiment of dispenser.
Figure 6:
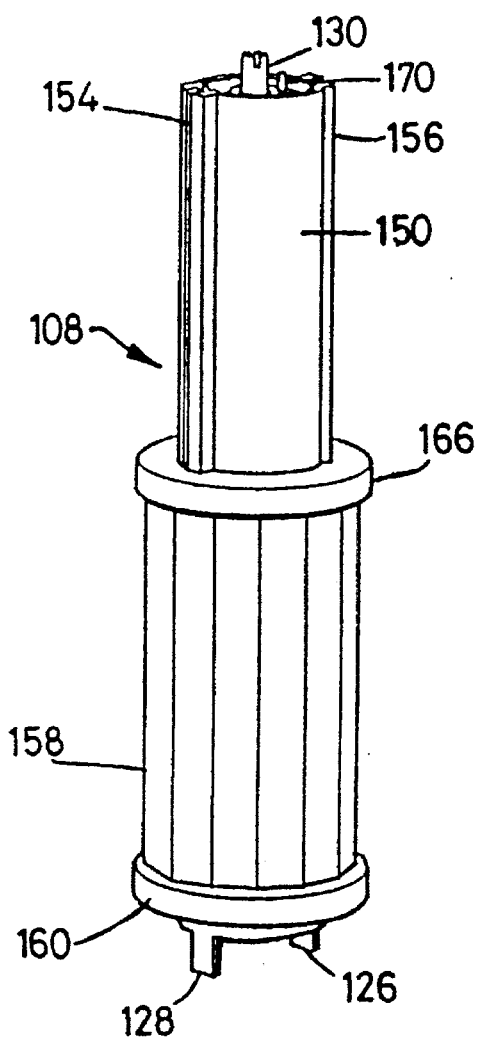
FIG. 6 shows the cartridge when assembled.

With reference to FIG. 1, the inhaler comprises a housing 100 which has a generally cylindrical portion and which is connected at its lower end to a mouth piece 102 extending substantially radially to the main body of the housing 100. The opposite end of the housing 100 includes a rotary member in the form of a cap 104 rotatably mounted on the rest of the housing 100. The cap 104 incorporates a window 106 through which a cartridge 108 contained within the body 100 can be viewed.

With reference to FIGS. 2 to 5, the cartridge 108 comprises a hollow cylindrical core 110 which has a reduced diameter upper portion 112 in which there is provided an upper aperture 114 and an integral tang 116. The core 110 also includes a lower portion 118 which is of a larger diameter than the portion 112, and which defines an annular shoulder 120 where it meets the portion 112. The portion 118 includes an external screw thread 122, a radial aperture 124 in its upper region, and two axially extending lower lugs 126 and 128.

The core 110 accommodates a vertical shaft 130, the upper part of which protrudes through the aperture 114. The top of the shaft 130 includes a slot 132 for engaging a protuberance 136 on the underside of the top of the cap 104 so as to provide a rotational key between the shaft 130 and the cap 104. The bottom of the shaft 130 is provided with a radial crank arm 138 which incorporates a radial slot 140 which slidably engages a boss 142 connected to a pin 144 positioned above a plate 146. The pin is in registry with an aperture (not shown) in the case 110 angularly spaced from the aperture 124.

The plate 146 is, with the cartridge assembled, attached to the interior of the core by suitable means (not shown), and the pin 144 and plate 146 include guide means (not shown) so arranged that rotation of the shaft 132 causes axial motion of the pin 144. With reference to FIG. 3, the shoulder 120 supports a sleeve 150 which is rotatably mounted on the core 110 and which surrounds the upper part 112.

The sleeve 150 includes internal longitudinal serrations 152 and two diametrically opposed sets of external longitudinal ribs 154 and 156.

With reference to FIG. 4, the medicament to be dispensed is contained in a tubular container 158 which has side walls which include a number of helically arranged radial through bores such as 159 (FIGS. 1 and 9), each of which contains a respective dose of material. The internal and external surfaces of the side walls are coated with corresponding sheets of a laminated foil which seals both ends of each bore.

The core 110 extends through the centre of the container 158 which includes a lower end cap 160 having a part helical groove (not shown) for engaging the thread 122, and an upper cap 162 which includes two diametrically opposed sets of slots 164 and 166 which engage the sets of ribs 154 and 156 to provide a rotational key between the sleeve 150 and the container 158.

The upper portion of the shaft 130 includes a shoulder 133 which supports a ratchet member 168 which is rotatable with respect to the shaft 130. The ratchet member 168 includes an upper boss 170 which engages in an arcuate track 172 (FIG. 7) in the underside of the cap 104 to provide a lost motion connection between the cap 104 and the ratchet member 168.

Figure 7:
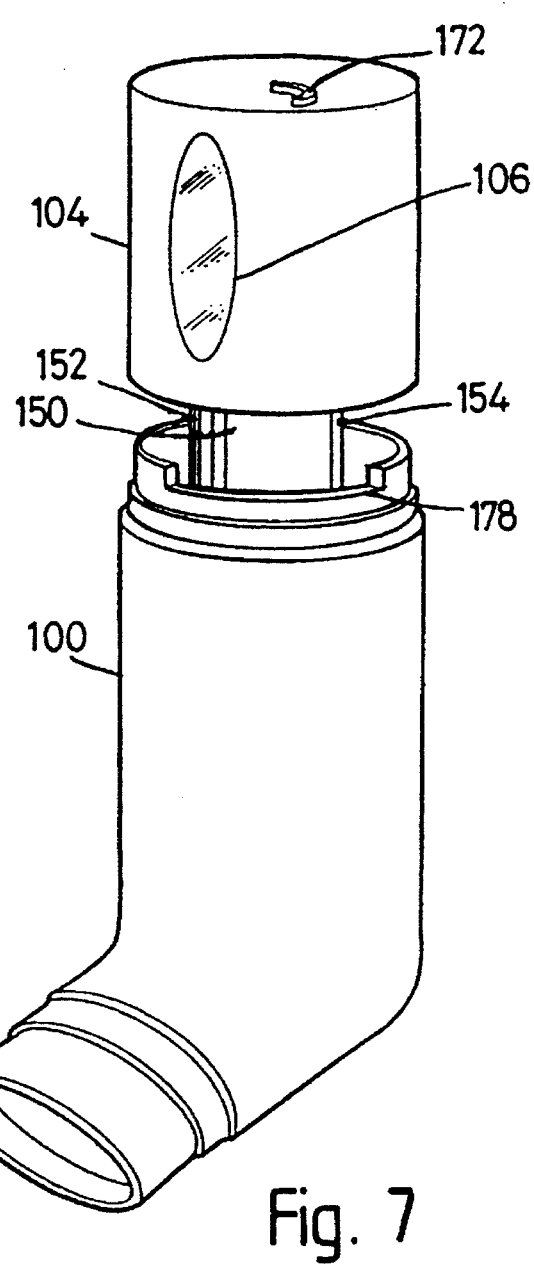
FIG. 7 is a diagrammatic partially exploded view of the cartridge and the housing.

As is illustrated in FIG. 7, the cap 104 is removable from the rest of the housing 100 to enable the assembled cartridge 108 to be inserted into the housing 100 until the lower lugs 126 and 128 of the core 110 engage in corresponding sockets 174, 176 (FIG. 1) in the bottom of the housing 100 to provide a rotational key between the core 110 and the housing 100.

As is illustrated in FIG. 7, the housing 100 includes an upper rebate 178 which cooperates with a downwardly projecting lug (not shown) in the cap 104 to provide stops which define the limits of allowable rotational movement of the cap 104 relative to the rest of the housing 100.

The lugs 126 and 128 space the lower end of the core 110 from the housing 100, thereby enabling the interior of the core 110 to communicate with an air inlet 180 provided in the underside of the mouthpiece 102, which includes an air outlet 182 partitioned from the inlet 180. The container 158 is spaced from the housing 100 so as to provide an outlet passage between vertical inner ribs 182 and 184 (FIG. 8a) which communicates with the outlet 182.

Thus the inhaler includes an airway, indicated by the marked arrows, extending from the air inlet 180 up through the core 110, through the aperture 124 and a dose containing through-bore in registry therewith and then through the outlet passage down to the outlet 182. In order to take a dose of medicament from the inhaler, the user must rotate the cap 104 from one to the other of its end positions and back again, causing the pin 144 to rupture the foil seal for a through bore and causing the through bore subsequently to be moved into registry with the outlet passage. This operation will now be described in greater detail with reference to FIGS. 8A–8F, and FIGS. 9A–9F.

Figure 8:
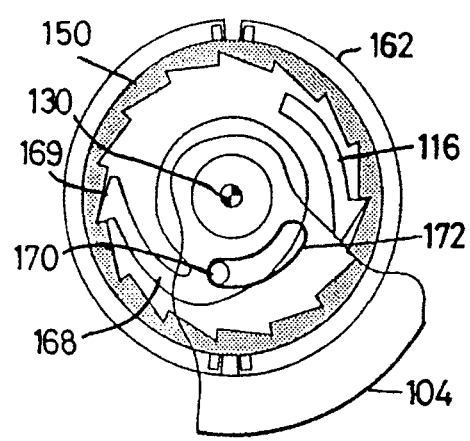
FIG. 8A–8F are diagrammatic sectional views illustrating the operation of part of the device, at various stages during cycle of operation of the device.
Figure 8:
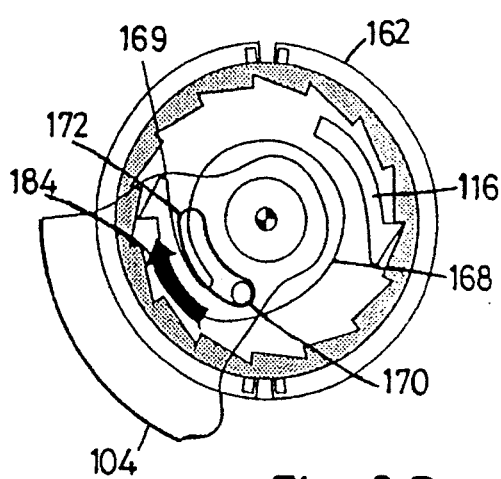
Figure 8:
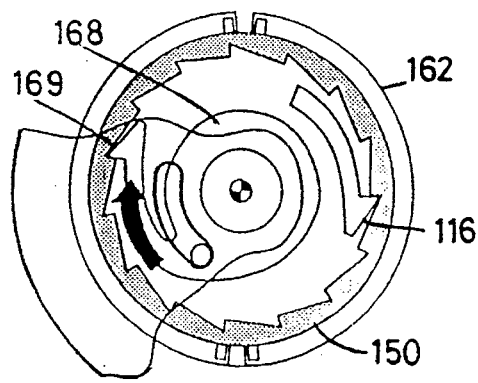
Figure 8:
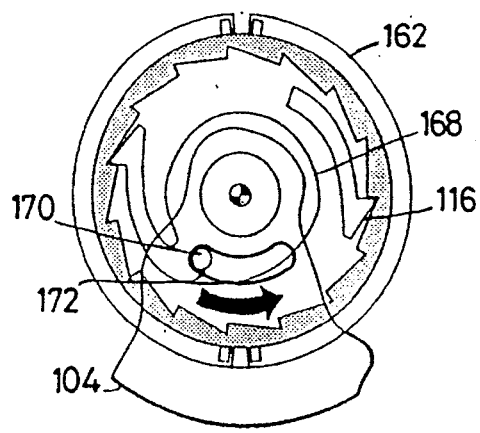
Figure 8:
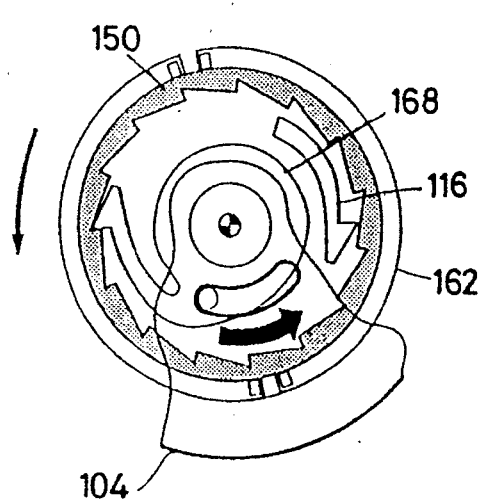
Figure 8:
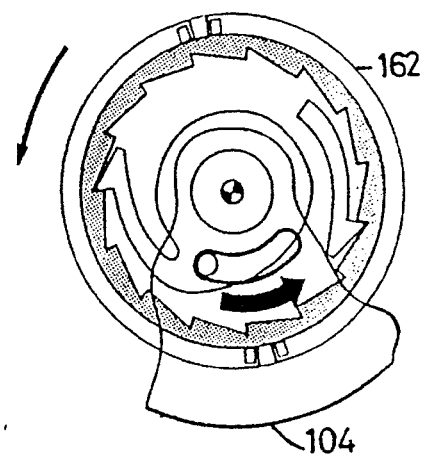
Figure 9A:
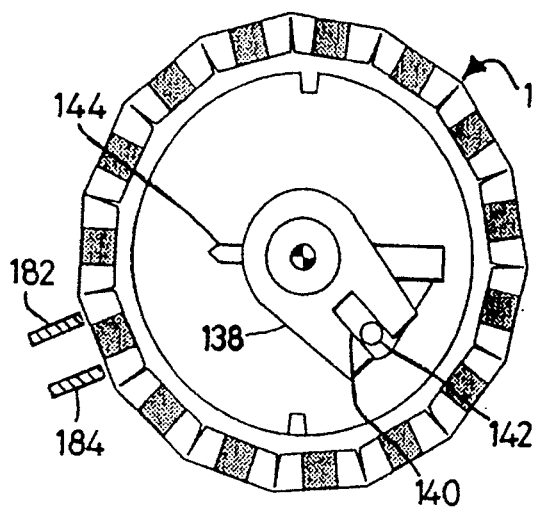
FIGS. 9A–9F are sectional views illustrating the operation of other parts of the device at corresponding stages in the operating cycle thereof.
Figure 9B:
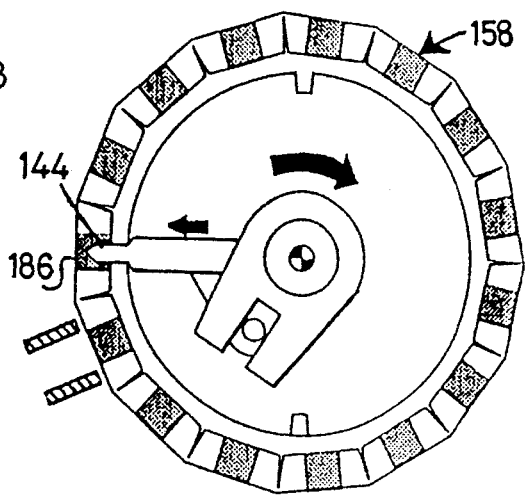
Figure 9C:
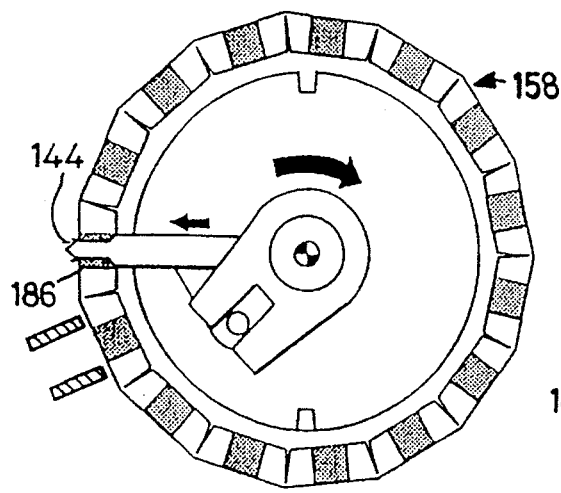
Figure 9D:
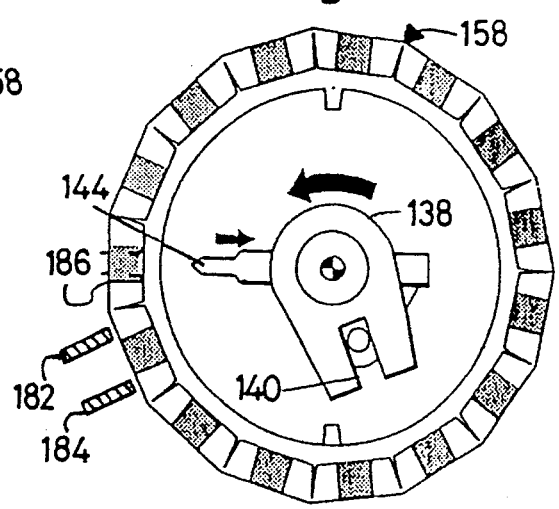
Figure 9E:
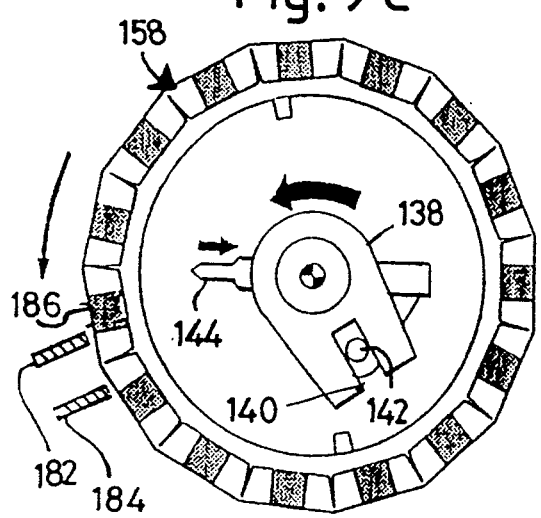

FIG. 8A shows the dispenser in a initial condition in which the pin 144 is retracted and all the compartments are sealed. Rotation of the knob 104 in a clockwise direction as indicated by the arrow 184 of FIG. 8B causes a corresponding rotation of the shaft 130 which, in turn, rotates the crank arm 138 so as to extend the pin 144 until it penetrates the inner seal of a cavity 186 (FIG. 9B). During this process, the slot 172 travels relative to the pin 170 so as to prevent rotation of the ratchet member 168 until the pin 170 engages the trailing end of the slot 172. Further rotation of the knob 104 in the same direction then also causes a corresponding rotation of the member 168 which can rotate relative to the sleeve 150 in a clockwise direction only. As this happens, the engagement of the tang 116 with the serrated inner edge of the sleeve 150 prevents the latter from rotating in an anticlockwise direction. When the limit of allowable clockwise rotation is reached, the member 168 is in the position shown in FIG. 8C and the pin 144 is in the position shown in FIG. 9C in which it extends through and beyond the bore 186 so as to pierce both inner and outer seals.

Figure 9F:
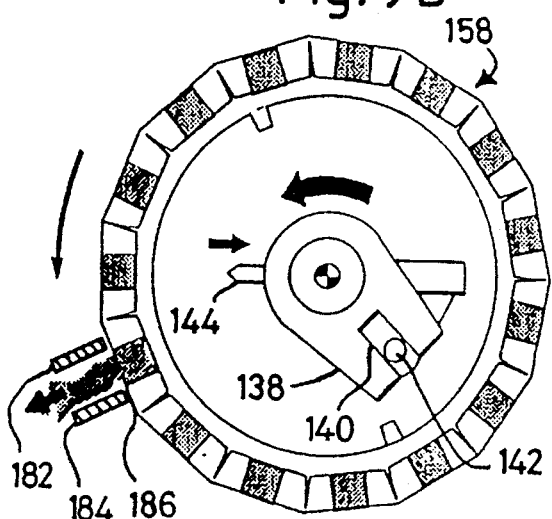

The knob 104 is then rotated in the opposite direction as shown in FIG. 8d, causing the pin 144 to be withdrawn from the bore 186. During the withdrawal of the pin 144, the slot 172 moves relative to the boss 170 so as to prevent corresponding movement of the sleeve 150 (and hence the container 158) until the pin 144 has been fully withdrawn. Further anticlockwise rotation of the knob 104 rotates the member 168, through the engagement of the boss 117 slot 172, in turn causing rotation of the sleeve 150. Since the latter is rotationally keyed to the container 158, this movement causes the container 158 to rotate on the lower portion 118 of the core 110, which in turn moves the through bores including the bore 186 along a part helical path as a result of the engagement of the cap 160 with the screw thread 122. By the time the knob 104 has reached the limit of allowable anticlockwise rotation, as illustrated in FIG. 8F, the bore 186 is in registry with the outlet passage (FIG. 9F).

If the user then inhales through the outlet 182 of the mouthpiece 102, the consequent airflow through the device expels medicament from the bore 186, into the outlet chamber and out through the outlet 182.

With reference to FIG. 1, the mouthpiece 102 also includes a grille 190 for capturing any loose fragments of the sealing foil which come adrift during inhalation.

The pin 144 is shown in more detail in FIGS. 15 and 16. The pin comprises a hollow cylindrical body 1 having an inclined forward edge 2 and an upper axial slot 3 extending from the top of the edge 2. As can be seen from FIG. 16, the edge 2 is substantially c-shaped when viewed end on. In use, the bottom of the edge 2 is the first portion of the pin 1 to penetrate the foil seals as the pin 1 is extended. The forward edge 2 creates a part circular incision in each of the foil seals to define two flaps. The portions of the foil aligned with the slot 3 are not cut, and therefore each define a hinge connecting a respective flap to the rest of the foil seal. As well as creating the flap, the pin 1 pushes the radial outer flap outwards as it is extended, and on retraction, pulls the radial inner flap inwards so that both flaps are moved away from the dose to be dispensed.

During the insertion of the pin 1 into a bore, little or none of the dose of material in the bore is expelled by the pin.

The danger of a user inadvertently taking an overdose by operating the cap a number of times before inhaling is avoided since material is ejected into the outlet passage only when the user inhales, and only from the bore in registry with the passage.

With reference to FIGS. 10A–H, the container comprises a body 1 which includes a number of through-bores, eg 2, for containing a respective dose of medicament. For the sake of clarity, the body illustrated in FIGS. 10A–H has only 16 such through-bores, although in practice a larger number of through bores may be present in the body 1.

With the container assembled, the body 1 is of a generally cylindrical shape, the bores being radially disposed, and the through bores are sealed by an outer sheet 4 and an inner sheet 6 of laminated foil attached to the body 1.

Figure 10A:
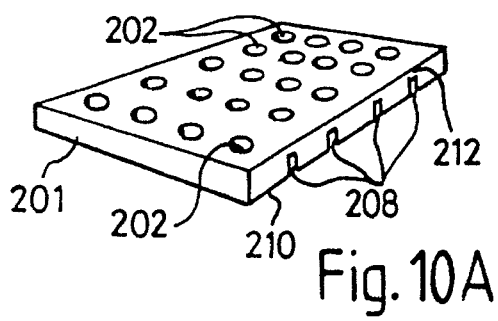
FIGS. 10A–10H are simplified diagrams showing various stages of a method of making a tubular container.

With reference to FIG. 10A, the body 1 is formed from a rectangular plate, also denoted by the reference number 1, of a plastics material, the underside of which includes a number of grooves 8 arranged in a regular parallel array. The grooves 8 divide the plate 1 into a number of parallel rigid strips, such as strip 10 running across the width of the plate, adjacent pairs of which are connected by corresponding reduced thickness portions, such as portion 12. The thickness of the plastics material constituting those portions is such that the adjacent strips are hingeable adjacent to each other. The through bores in the plate 1 are all provided in the strips.

Figure 10B:
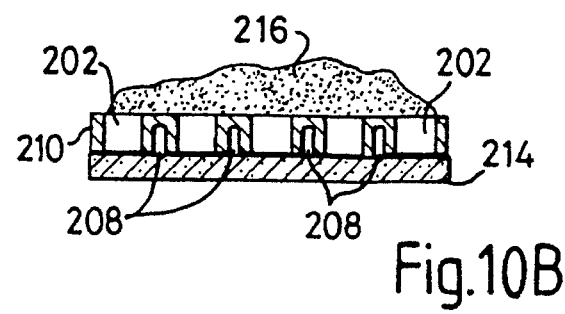

Turning to FIG. 10B, the plate 1 is placed on a bed 14 of a porous material, with the non grooved face of the plate upper most, and the upper surface of the plate 1 is covered with a layer of powdered medicament 16, which covers one end of each of the through bores in the plate 1.

Figure 10C:
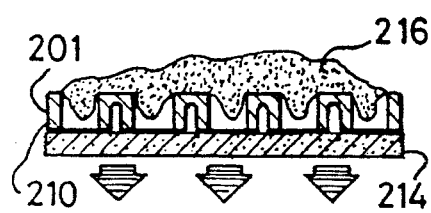

With reference to FIG. 10C, air is then blown through bores and the bed 14, causing the material 16 to be sucked into each of the through bores. The porosity of the bed 14 is such that it is impervious to the material 16. As a result, the bed 14 prevents material 16 being discharged from the through bores to the lower end thereof.

Figure 10D:
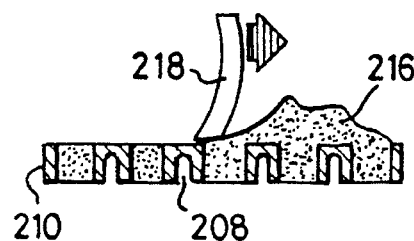
Figure 10E:
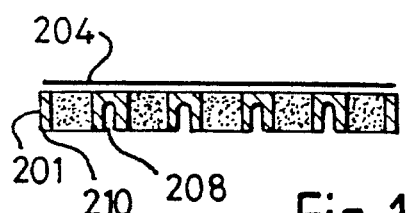
Figure 10F:
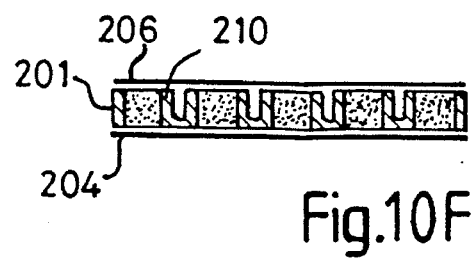
Figure 10G:
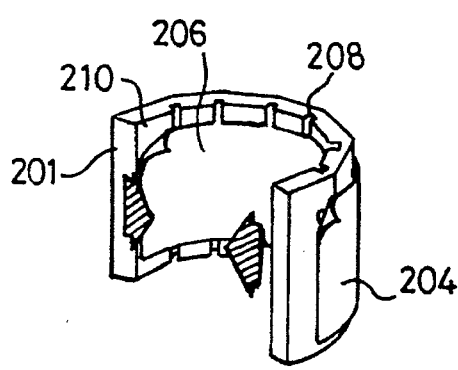
Figure 10H:
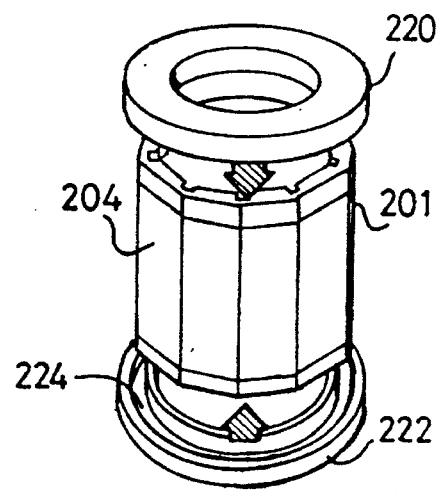

When the through bores have been filled with the material 16, any excess material which has not been drawn into a through bore is removed by drawing a resiliently flexible blade 18 across the upper surface of the plate 1 (FIG. 10D). The sheet is then heat sealed onto the upper surface of the plate 1 (FIG. 10E), which is then inverted so that the sheet 6 can be similarly applied to the opposite face of the plate 1 (FIG. 10F).

The flexibility provided by the reduced thickness portions between the strips of the plate 1 enable the latter to be rolled (FIG. 10G) to a generally cylindrical shape, with the strips extending axially along the cylinder, and the grooves 8 on the inner surface thereof, so as to form the body 1.

Once the body 1 has been formed two ring-shaped end caps 20 and 22 are applied one at each end of the cylinder. Each cap includes an annular track, such as track 24, into which the strips extend and in which the strips are a tight fit. Thus the caps 20 and 22 prevent the body 1 from unravelling. The components shown in FIGS. 11A–11E correspond with those shown in FIGS. 11A–H, and corresponding components are indicated by the same reference number raised by 30. Thus the container comprises a cylindrical body 31 formed from a plate (also referenced 31) having a number of through-bores eg 32 which are filled with powdered medicament by means of the same method as illustrated in FIG. 10, and are then sealed on one side by a first sheet of laminated foil 34 and on the other side by a second sheet of laminated foil 36 applied to the body 31 after the latter has been inverted.

It will be seen that the body 31 contains a larger number of through-bores, eg 32, than the body 1, and can therefore contain a greater number of doses of medicament than the body 1. In addition each of the grooves in the body 31, eg groove 38, is tapered so as to facilitate the rolling of the plate 31. The caps 50 and 52 each include diametrically opposed inner slot arrangements, for example 56 and 58 which enable the container to be rotationally keyed to the rotational core or an inhaler in which the container is to be used.

Figure 11A:
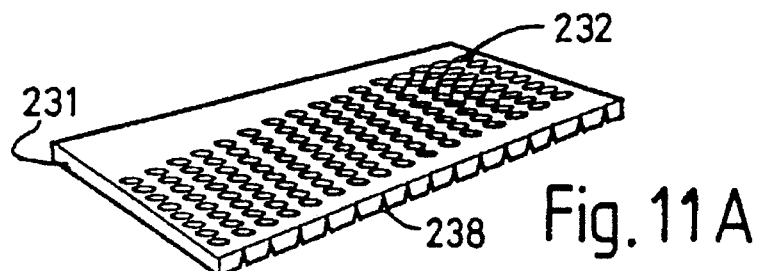
FIGS. 11A–11E show components of an alternative type of tubular container which can be filled by the method illustrated in FIGS. 10A–F, FIG. 13 showing the container when assembled.
Figure 11B:
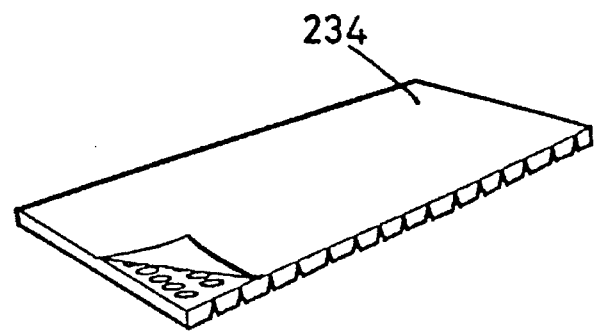
Figure 11C:
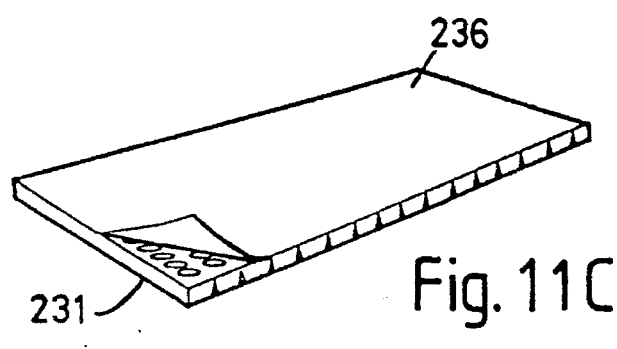
Figure 11D:
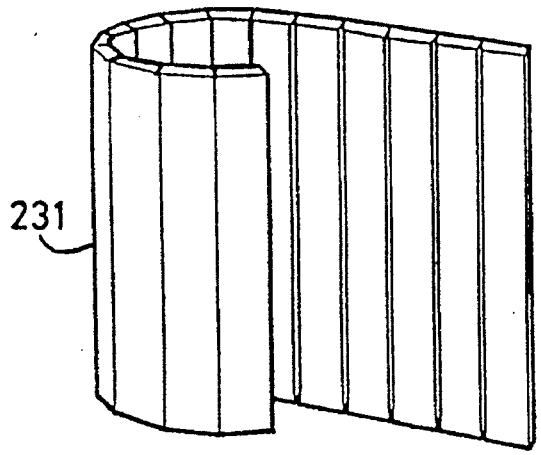
Figure 11E:
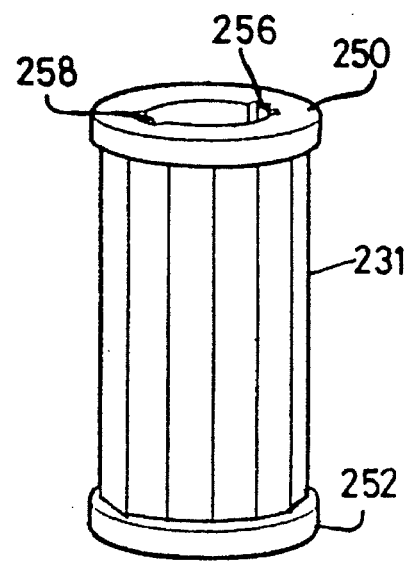

As can be seen from FIG. 11A, the through-bores are so arranged as to lie on a helical path on the body 31, when the container is assembled.

Figure 13:
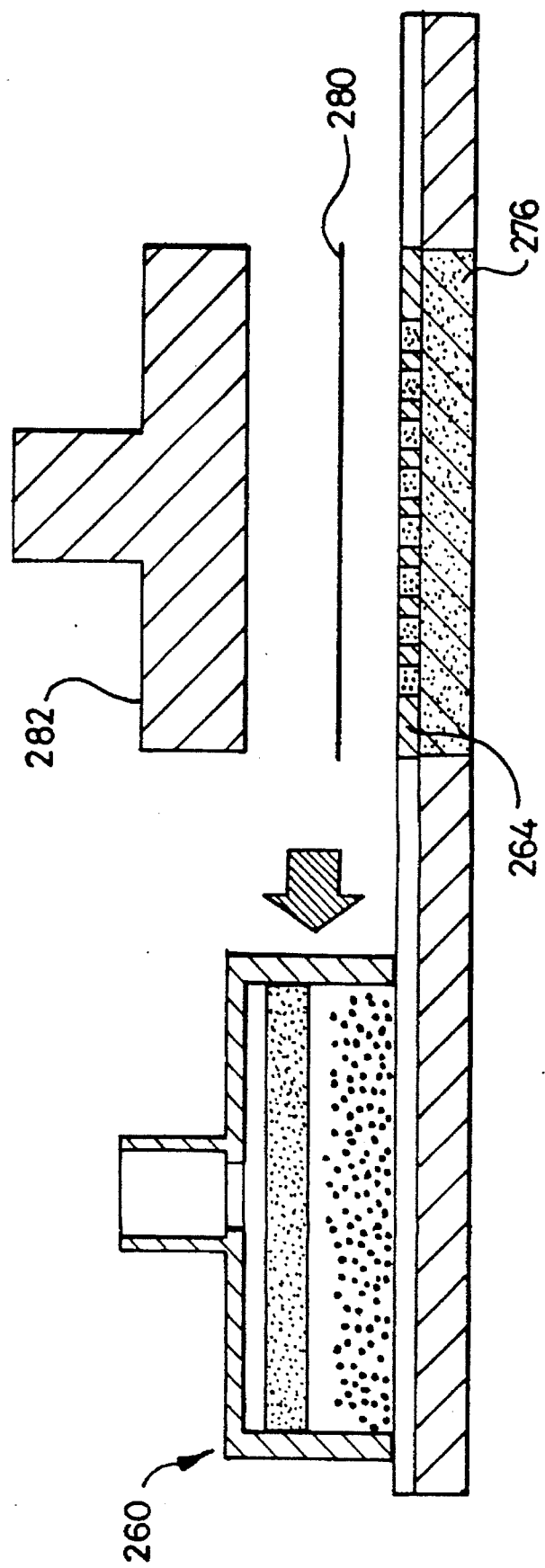
FIG. 13 shows the apparatus of FIG. 12 when being used to seal one side of the container, in accordance with a subsequent method step.

With reference to FIG. 13, apparatus for filling the container includes a filling station at which there is provided a filling head 260 comprising a rectangular upper plate 262 of corresponding dimension to a plate 264 to constitute a cylindrical body. Vertical peripheral walls 266 extend from the plate 262 to the plate 264 so that the head 260 and plate 264 define a filling chamber 268. The plate 262 includes a central aperture 270 which communicates with a air inlet 272. The chamber 268 contains a diffuser 274 positioned between the aperture 270 and the plate 264. The head includes a further inlet (not shown) through which powdered material is introduced into the chamber 268 between the diffuser 274 and the plate 264.

In use, air is introduced into the chamber 268 through the aperture 270, fluidising the powdered material in the chamber 268 and increasing the air pressure in the chamber. The increase in air pressure causes air to flow out of the chamber through the through-bores in the plate 264 and through a porous bed 276 on which the plate 264 is supported.

This flow of air draws material into the through-bores, thereby filling the latter.

The diffuser 274 ensures an even flow of air over the powder bed, so as to avoid any tendency for the incoming air to blow a hole in the powder. The diffuser 274 and bed 276 are of a similar porous material.

Figure 12:
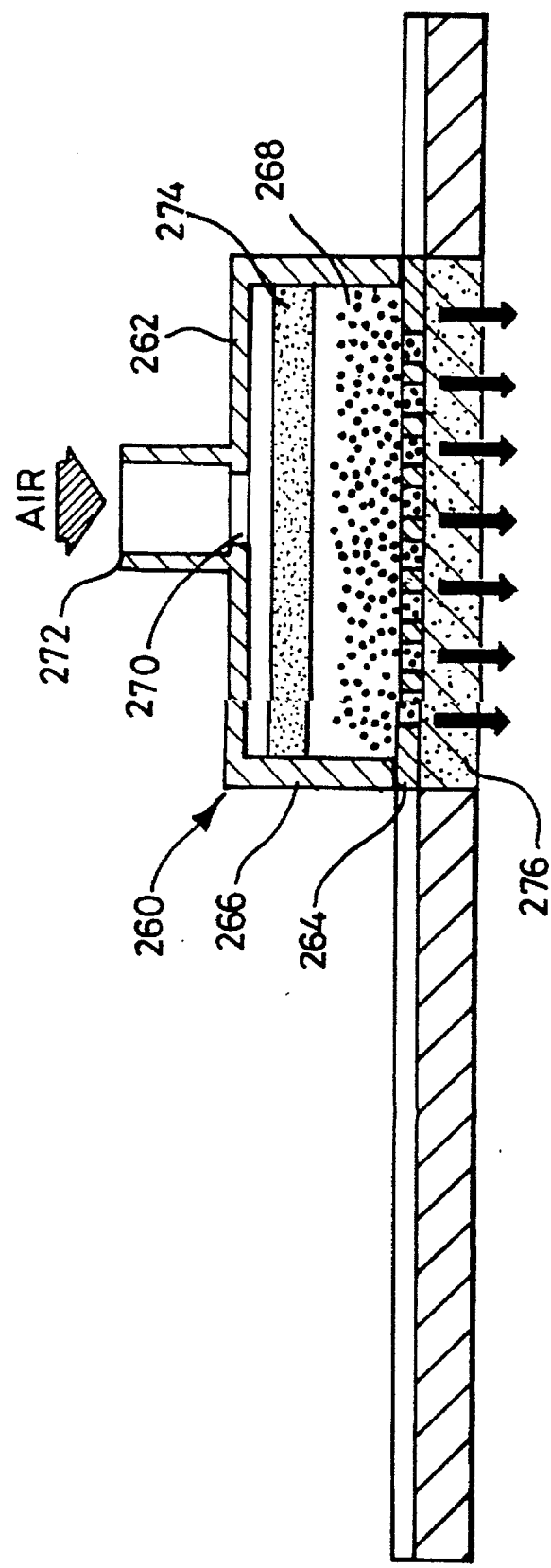
FIG. 12 is a diagrammatic sectional side view of apparatus for filling the containers shown in FIGS. 10 and 11, in the course of one stage of the method.

As is shown in FIG. 12, the head 260 is then moved laterally away from the plate 264, and a sheet of foil sealing material 280 is positioned over the plate 264 by foil supply means (not shown) an upper heater block 282 is also moved into registry with the plate 264 and is then lowered vertically onto the foil 280 and plate 264 so as to seal the foil 280 onto the plate.

The apparatus includes means (not shown) for inverting the plate 264 to enable a sheet of foil to be applied to the opposite side in the same way, and means for rolling the plate 264 to form a cylindrical body.

Figure 14:
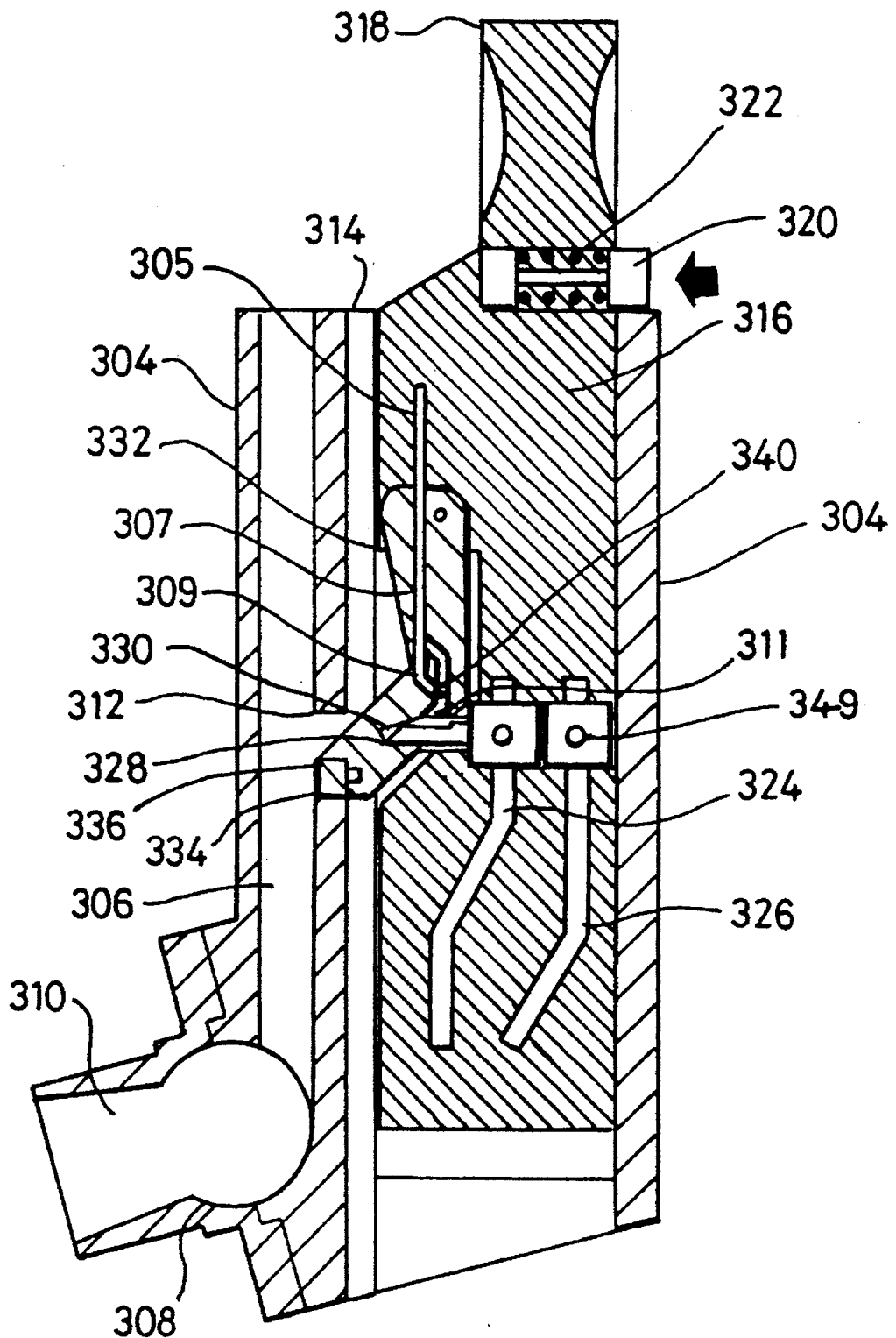
FIG. 14 is a sectional side view of the second embodiment of dispenser.
Figure 22:
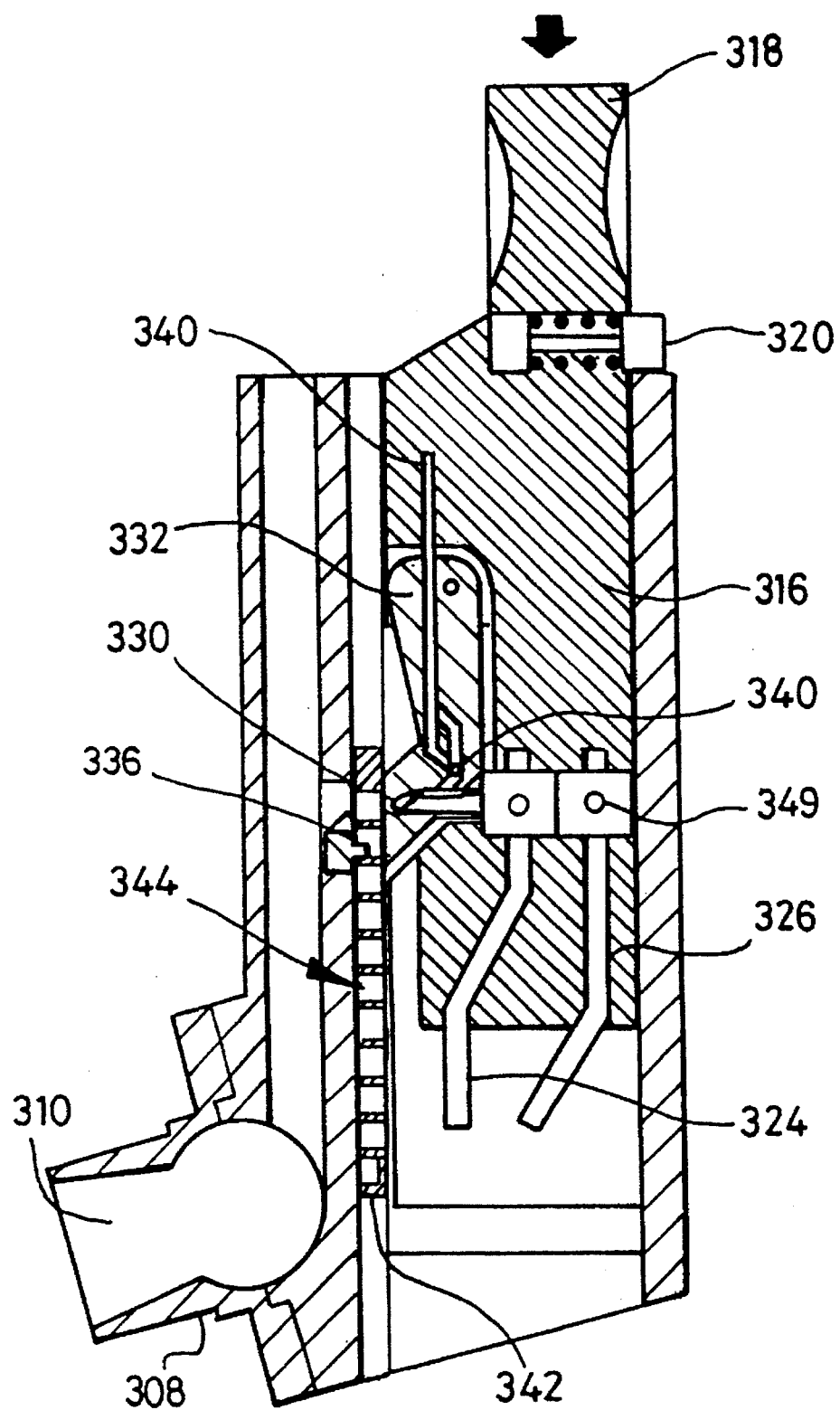
Figure 23:
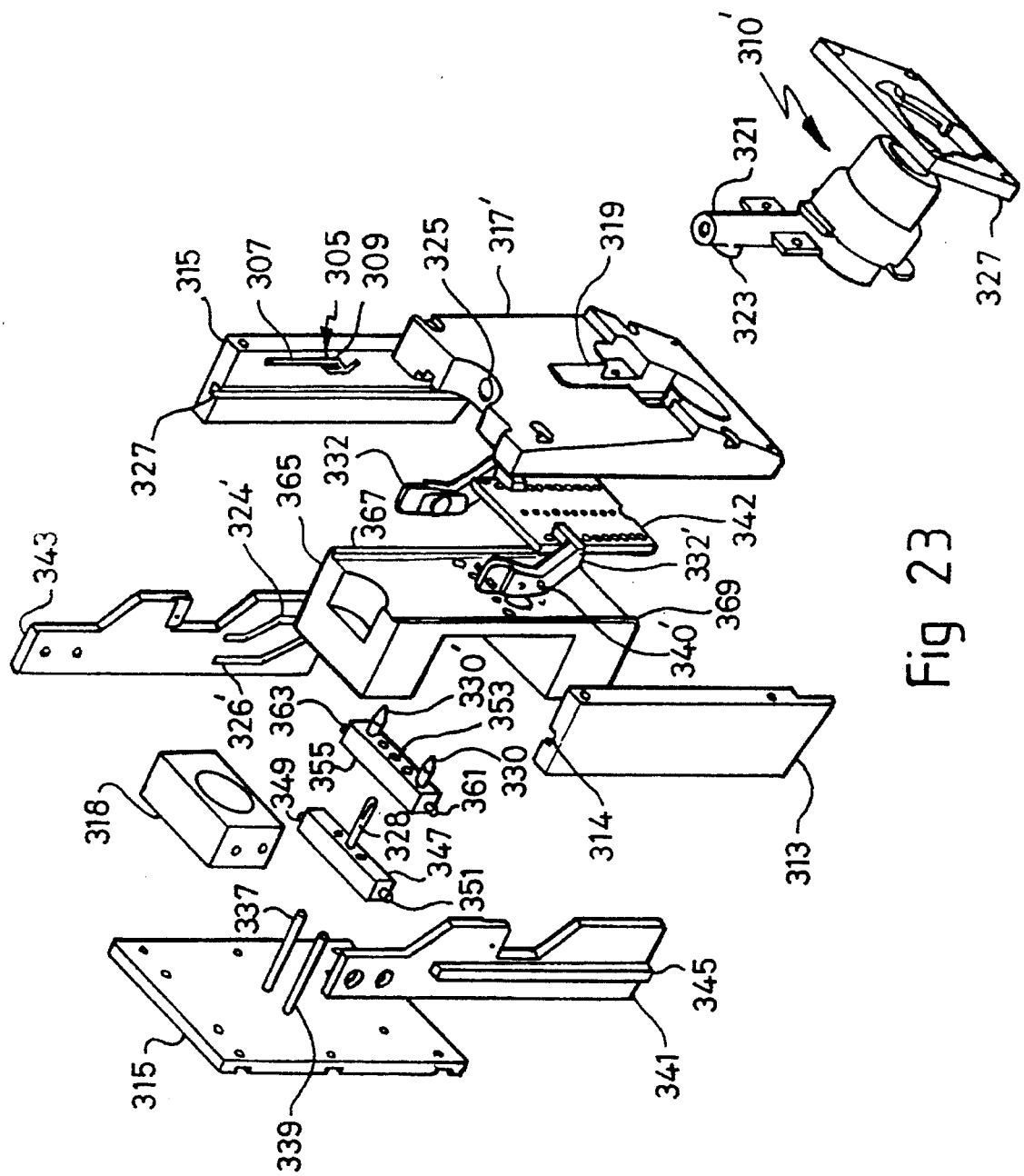
FIG. 23 is an exploded perspective view of the second embodiment, showing a slight modification to a part thereof.

With reference to FIGS. 14 and 23, the second embodiment of dispenser comprises a rectangular section housing 304, which, in both versions includes a back plate 315 from which a pair of guide rods 337 and 339 project, and a pair of opposed side plates 313 and 315. In the version of the second embodiment shown in FIGS. 18 to 22 the housing 304 has a front plate 317 in which there is formed a passage 306 which is sealed at its top, and which communicates at its bottom with a vortex chamber 308 forming part of a mouthpiece 310. The passage 306 also communicates with an opening 312 part way along its length. As shown in FIG. 23, an alternative front plate 317' for the housing has a recess 319 which accommodates a tube 321 forming part of a separate mouthpiece assembly 310'.

The tube 321 has a side opening 323 which corresponds in position and function to the opening 312. The tube 321 is also open at its top and communicates with a vertical passage in the plate 317' which passage terminates in an opening 325. A plate 327 holds the mouthpiece assembly 310' on the plate 317'. In all other respects the version shown in FIG. 23 is the same as that shown in FIGS. 18 to 22 and the same reference numbers are therefore used to denote the same components.

Each of the side plates 313 and 315 includes a guide track, 314 and 327 respectively, which run from top to bottom of the housing, and which, in use, helps to locate a slider, described below.

The plates 313 and 315 are also formed with guide tracks, one of which is shown at 305 (superimposed on other components in FIGS. 18 to 22), each of which has a vertical portion 307 and a lower portion in the form of a circuit 309. Each track also terminates in an inclined portion 311. The housing 304 also accommodates a hollow rectangular section slider member 316 which terminates in an upper handle 318. A button 320 is mounted at the base of the handle 318, and is outwardly biased, into the position shown in FIG. 14 by a compression spring 322.

The slider comprises a pair of side plates 341 and 343 each of which has an outer vertical rib, one of which is shown at 345, which is slidably located in a respective one of the tracks 314 and 327. The plate 343 has two cam tracks 324' and 326' each of which is aligned with a respective identical track (324 and 326) in the plate 341.

A bar 347 has one end boss 349 which extends into the track 326' and, at its opposite end, a boss 351 which extends into the track 326. A piercing pin 328, of the kind shown in FIGS. 15 and 16, projects from the centre of the bar 347, and through a hole 353 in another bar 355. The bar 355 carries location pins 330 and 330' which flank the pin 328. The bar also has opposed end bosses 361 and 363, each of which extends into a respective one of the tracks 325 and 324'.

The bars 347 and 355 are both slidably supported on the rods 337 and 339.

The slider 316 also carries a pair of indexing arms 332 and 332', which are each pivoted to a respective one of plates 341 and 343 and are positioned one on either side of the pins 330, 330' and the piercing pin 328. Each indexing arm has an outboard end 334 which includes a finger 336. The outboard ends of the indexing arms flank the passage 306, and each arm has a boss, 340 and 340' respectively, which engages in either the track 305 or the corresponding opposite track in the housing plate 313.

The housing also contains a central block 365 having apertures through which the pins 330, 330' and 328 can extend. The block also has two opposed side ribs 367 and 369 which act as a guide for a container to be used with the inhaler.

For the sake of clarity, the sectional views in FIGS. 18 to 22, are taken in two planes; sections of the plate 343 and arm 332 have been taken in the plane of the plate 343, whilst the section of the button 318 and housing 304 is taken in a vertical plane which bisects the inhaler. In addition, the pin 328 and bar 347 have been superimposed on the sectional views, as have the bar 355 and pin 330.

The container for use in this dispenser comprises a plate 342 which includes a central column of ten apertures 344 each of which contains a respective dose of material. As can be seen from the detail 346, each aperture has a flattened edge portion, for example 348. With the container received in the dispenser, the flattened edge portions constitute the tops of the apertures. The row of apertures 344 is flanked by two rows 340 and 352 of further apertures which are used by the dispenser to locate and index the container.

Figure 18:
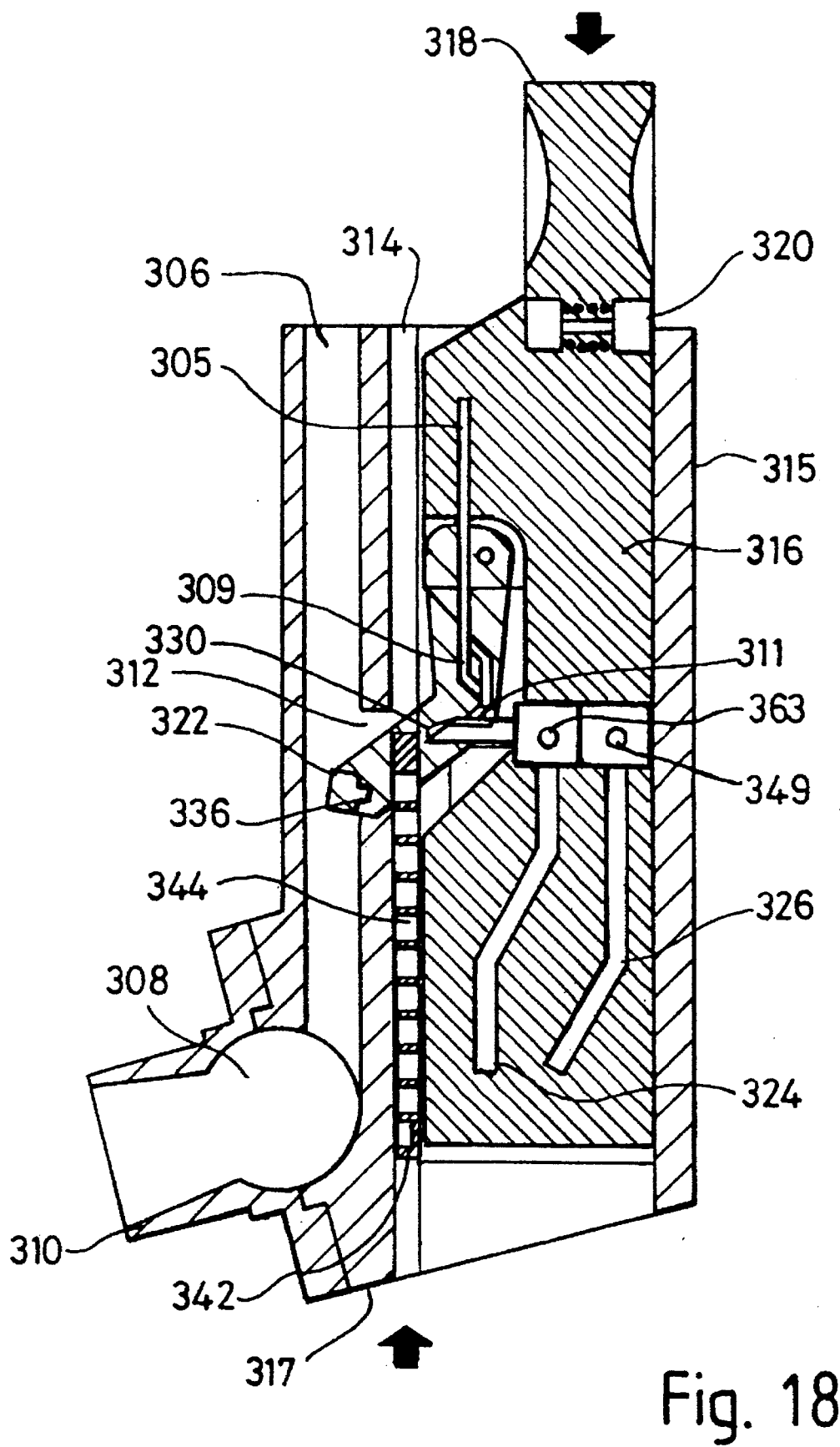
FIGS. 18–22 are views which correspond to FIG. 14 and which show the dispenser (with a container therein) at various stages in its cycle of operation.

Two strips of foil laminate (not shown) are bonded to opposite sides of the container to seal the apertures in the column 344. In order for the dispenser to be able to receive the container, the indexing arms 332 and 332' have to be swung clear of the region of the dispenser to be occupied by the container. To that end, the button 320 is depressed, and the slider 316 is pushed down, which causes the locating protuberance on each arm to move along the inclined bottom portion of the respective track. This in turn causes the indexing arms to pivot in a clockwise direction until the position shown in FIG. 18 is reached, in which the finger (for example 336) on each arm is laterally spaced from the track 314 and the opposite track in the housing. The container 342 can then be inserted into the bottom of the housing and pushed along the tracks to the position shown in FIG. 18.

Figure 19:
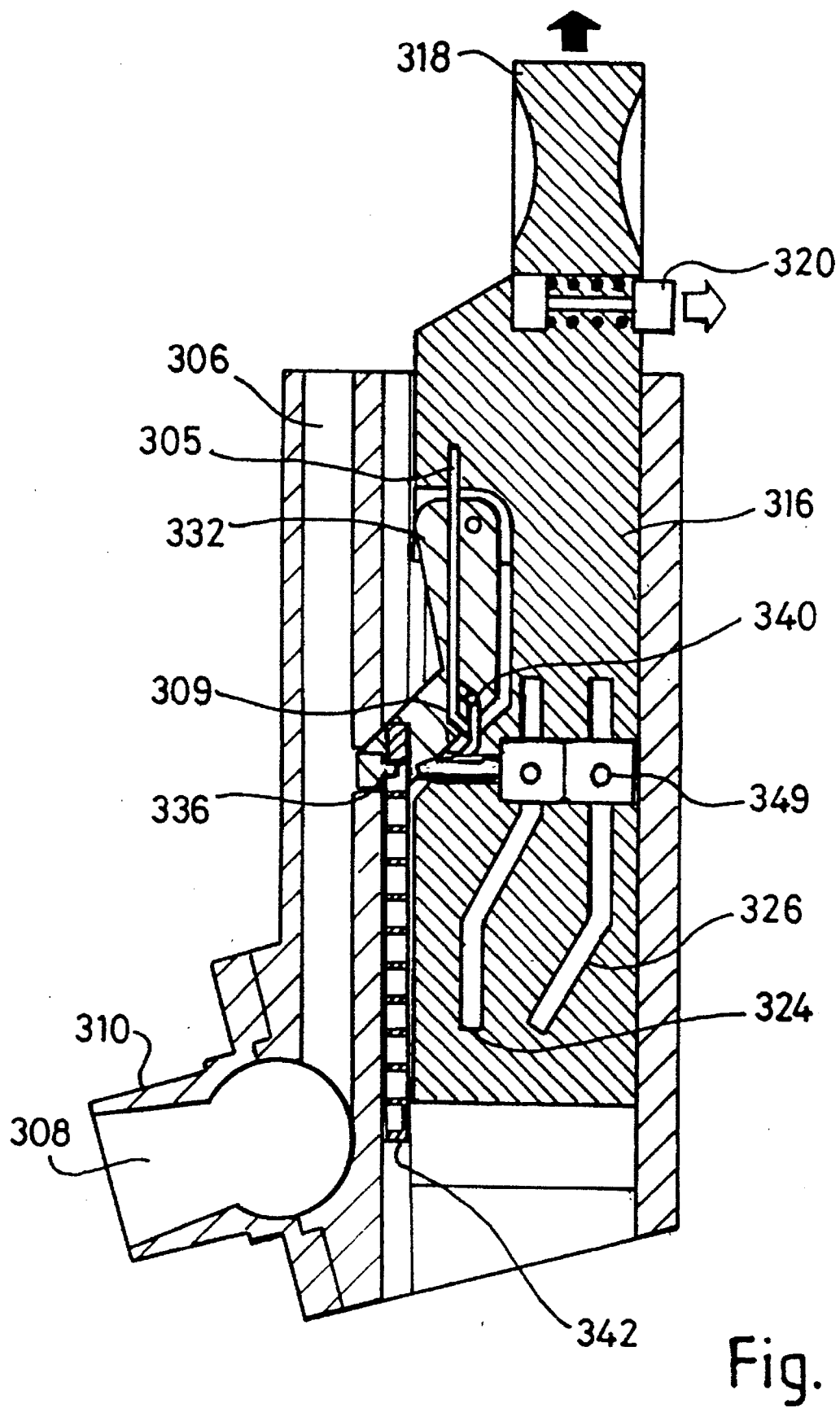
Figure 20:
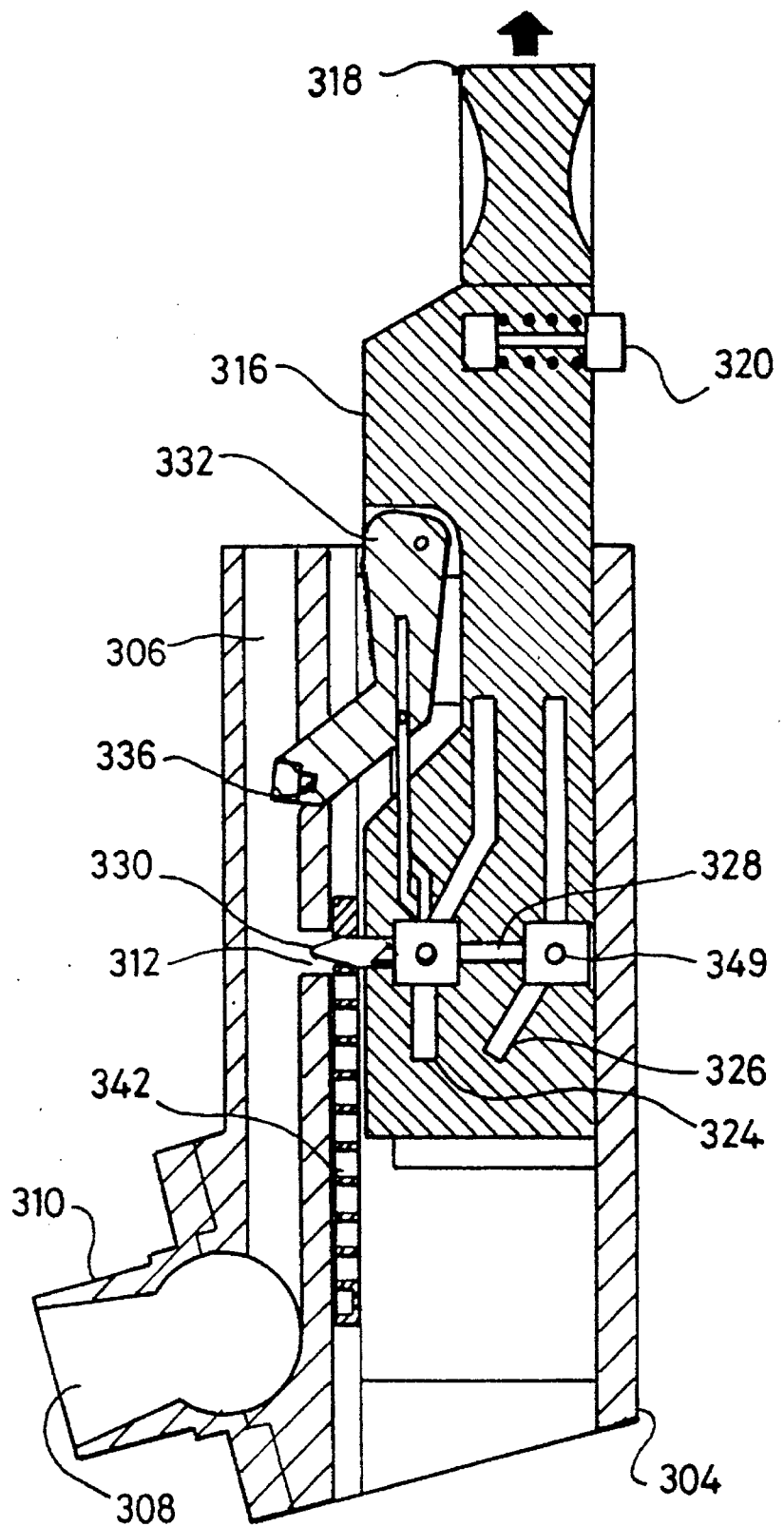
Figure 21:
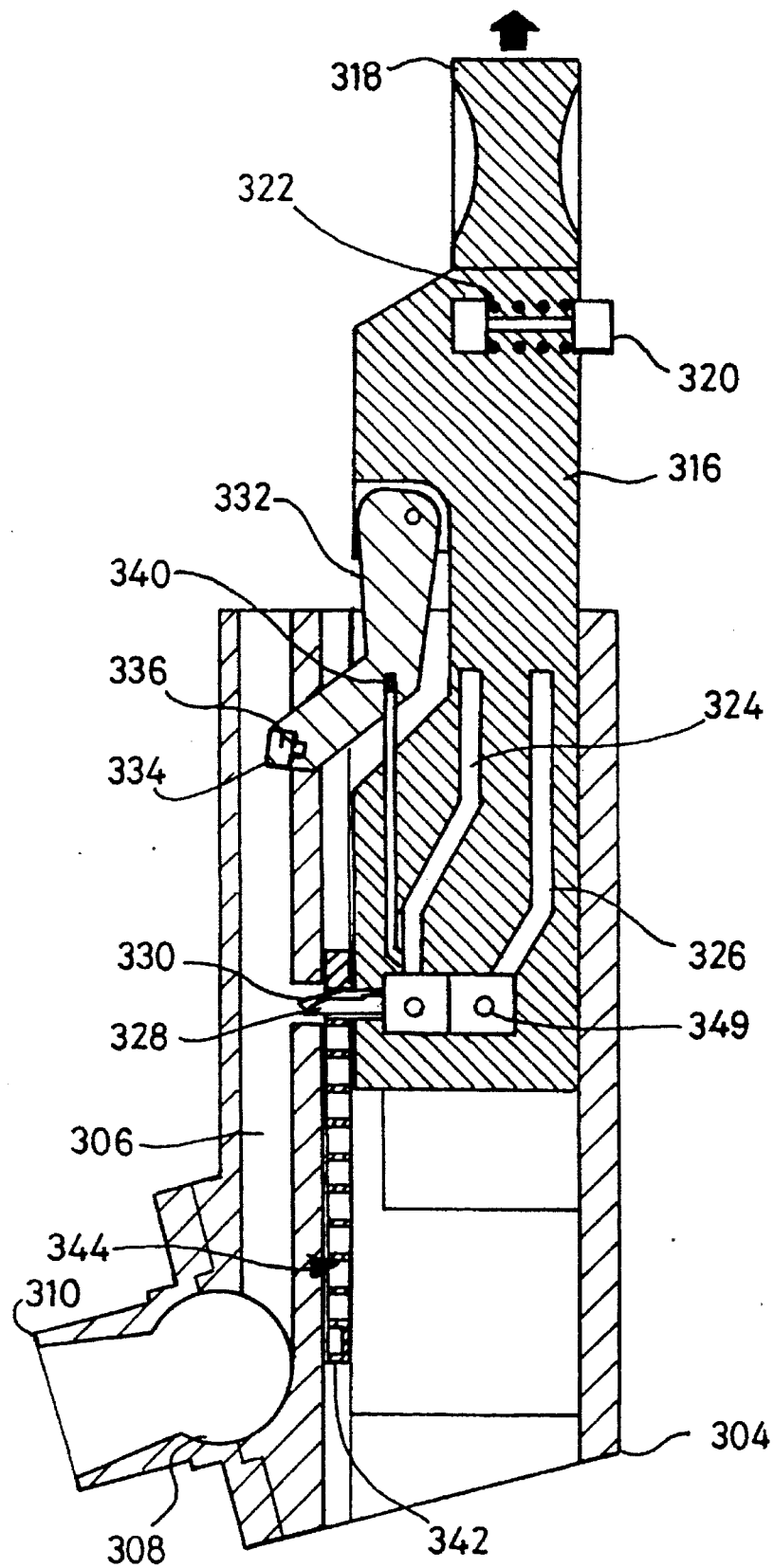

With reference to FIG. 19, the slider 316 is then raised, causing the button 320 to pop out as it moves clear of the housing 304. As this happens, the protuberance on each indexing arm moves up from the inclined bottom portion of its respective track into the right hand side (as viewed in the Figures) portion of the circuit 309 of the track. As a result, both indexing arms pivot in a clockwise direction until the fingers at the ends of the arms locate in respective holes at the top of the columns 344 and 352 of the container 342. Continued upward movement of the slider 316 therefore draws the container 342 up the housing until the position shown in FIG. 19 is reached, in which the top dose containing aperture of the column 344 is in registry with the piercing pin 328.

As the user continues to lift the slider 318, the boss on each of the indexing arms travels from the circuit portion of its respective track into the vertical portion thereof, causing the indexing arms to move in an anti-clockwise direction until the fingers at the outboard ends of the arms are disengaged from their respective location holes.

Raising the slider 316 also moves the camming tracks 324, 324' 326 and 326' relative to the bars 347 and 355. As can be seen from the Figures, the shapes of the tracks are such that upward movement of the slider first extends the location pins, 330 and 330', until they extend into the holes previously occupied by the fingers on the ends of the indexing arms to retain the container in a position in which the top dose containing aperture is in registry with both the pin 328 and the opening 312 in the passage 306.

As the user continues to raise the slider 316, the tracks 326 and 326' cause the piercing pin 328 to be extended through the dose containing aperture, thus piercing the foil seals on either side thereof.

The user then lowers the slider into the position shown in FIG. 22 which returns the bosses (for example 340) on the indexing arms to the positions shown in FIG. 14 via the lefthand side of the circuit portions of their respective tracks, so that the fingers on the ends of the indexing arms engage the next location holes down from the ones previously engaged. This movement also retracts pins 328, 330 and 330'. The user can then administer the dose of material from the first of the central apertures by inhaling through the mouthpiece 310.

The circuit portions of the tracks which move the index arms (eg track 305) have a number of one way gates to ensure that the boss (340, 340') of each arm always moves around the respective circuit in the same sense.

As the user does this, air is drawn through the bottom of the housing 304, the centre of the slider 316 and through the opening 312, via the dose containing aperture in registry therewith. The vortex chamber 308 helps to provide a reasonably even distribution of medicament in the flow of air through the mouthpiece 310.

The next time a dose is required, the user raises the slider 316 which indexes the container up through the dispenser so that the next dose containing hole is brought into registry with the opening 312 and its seals pierced by the pin 328.

This process is repeated until all the doses contained in the container have been inhaled, whereupon the container can be removed from the top of the housing 304.

It will be seen that, in use, the button 320 acts as a stop for limiting the amount of downward movement of the slider 316 when a container is not to be loaded into the housing.

We claim:

1. A device for dispensing single doses of a powdered medicament from a container having a plurality of apertures, each of which holds a respective one of said doses, and is sealed by two opposed seals, the device comprising a housing for holding the container, the housing having an outlet and an airway which communicates with the outlet, and being configured to allow the container, to move relative thereto to bring each aperture in succession into registry with the airway, wherein the device includes a piercing member moveable from a retracted position in which it is positioned clear of the container into an extended position in which it extends through the aperture, said movement causing the piercing member to rapture the seals, and wherein the piercing member has a relatively small cross-sectional area compared with that of each aperture so that said movement of the piercing member expels substantially no medicament from the aperture.

2. A device according to claim 1 in which the piercing member comprises a hollow pin.

3. A device according to claim 1 in which the pin is so shaped as to create in the seals flaps which hinge away from the aperture to allow the contents thereof to be discharged.

4. A device according to claim 3 in which the forward end of the pin is substantially c-shaped when viewed end on.

5. A device according to claim 1 in which the device includes a common actuation member linked both to the piercing member and to indexing means for bringing each aperture in succession into registry with the airway, the arrangement being such that manipulation of the actuating member by the user both operates the indexing means and ruptures the seal of an aperture.

6. A device according to claim 1 in which the piercing member is so positioned as to rupture the seals of an aperture while the latter is in registry with the airway.

7. Apparatus comprising a device according to claim 1 and a container having a plurality of sealed apertures each holding a respective dose of medicament, the container being held within the housing of the device and being moveable to bring each aperture in succession into registry with the airway, the piercing member of the device being operable to rupture the seals of each aperture whilst expelling substantially no medicament therefrom.

8. Apparatus according to claim 7 in which the apertures are all sealed by two opposed pieces of sheet material bonded to a container.

9. Apparatus according to claims 7 when appended to claim 3 in which each aperture in the container is flattened in the region in which the hinges of the flaps are formed.

10. Apparatus according to claim 7 in which the container is cylindrical, and the actuating member comprises a rotary member, rotation of which alternately indexes the container and causes the pin to break the seals of an aperture.

11. Apparatus according to claim 10 in which there is provided stop means for defining the maximum extent of allowable rotation of the rotary member.

12. Apparatus according to claim 11 in which rotation of the rotary member from one to the other of the two positions defined by the end stops causes the pin to pierce a seal, whilst rotation of the rotary member in the opposite sense into said one position causes the container to be indexed.

13. Apparatus according to claim 10 in which the piercing member is situated within the volume defined by the inner periphery of the cylindrical container.

14. Apparatus according to claim 10 in which the rotary member is connected to the container through lost motion means so arranged as to prevent container from being rotated by the rotary member while the piercing member is being inserted into or withdrawn from an aperture.

15. A cartridge for use in apparatus according to claims 10, the cartridge comprising a container for containing said doses and incorporating the piercing member and means for indexing the container.

* * * * *